United States Patent
Suzuki et al.

(10) Patent No.: US 6,310,100 B1
(45) Date of Patent: Oct. 30, 2001

(54) METHOD OF TREATING HYPERTENSION

(75) Inventors: Atsushi Suzuki; Ryuji Ochiai; Ichiro Tokimitsu, all of Tochigi (JP)

(73) Assignee: KAO Corporation, Tokyo (JP)

(*) Notice: Subject to any disclaimer, the term of this patent is extended or adjusted under 35 U.S.C. 154(b) by 18 days.

(21) Appl. No.: 09/667,794

(22) Filed: Sep. 22, 2000

(30) Foreign Application Priority Data

Sep. 22, 1999 (JP) .................................................. 11-268461
Jul. 31, 2000 (JP) .................................................. 12-230463

(51) Int. Cl.$^7$ .................................................. A61K 31/19
(52) U.S. Cl. .............................................................. 514/570
(58) Field of Search ............................................... 514/570

(56) References Cited

U.S. PATENT DOCUMENTS

| | | | | |
|---|---|---|---|---|
| 5,108,750 | * | 4/1992 | Liu | 424/195.1 |
| 5,288,902 | * | 2/1994 | Taniguchi et al. | 562/478 |
| 6,020,020 | * | 2/2000 | Cain et al. | 426/601 |
| 6,025,348 | | 2/2000 | Goto et al. . | |
| 6,139,897 | | 10/2000 | Goto et al. . | |

OTHER PUBLICATIONS

R. L. Heppolette, et al., Chemistry and Industry, pp. 1457–1458, "SO$_2$X Compunds In Aromatic Nucleophilic Substitution," Nov. 20, 1954.

H. J. Klosterman et al., J. Am. Chem. Soc, vol. 81, pp. 2188–2191, "The Glucosides Of Flaxseed. II. Linocaffein," May 5, 1959.

R. Adams, et al. Journal of American Chemical Society, vol. 74, pp. 5346–5348, "Preparation And Reactions Of o–Hydroxycinnamic Acids Esters," Nov. 5, 1952.

* cited by examiner

Primary Examiner—Raymond Henley, III

(57) ABSTRACT

A method for treating hypertension, a cardiac disease, or a cerebrovascular disease comprising administration of ferulic acid or a derivative thereof, to a subject in need of treatment. Therapeutic compositions comprising ferulic acid and its derivatives may comprise pharmaceutical products, nutritional supplements or products, and foods. Such compositions may further comprising diglycerides in combination with ferulic acid and its derivatives.

11 Claims, No Drawings

METHOD OF TREATING HYPERTENSION

BACKGROUND OF THE INVENTION

1. Field of the Invention

The present invention is directed to methods of treating diseases such as hypertension using ferulic acid compounds. It also relates to compositions, such as fat compositions, comprising a ferulic acid compound and a diglyceride.

2. Description of the Background Art

Hypertension is correlated with cardiac diseases such as angina pectoris, myocardial infarction and heart failure. It also is associated with cerebrovascular diseases such as cerebral infarction, cerebral hemorrhage and subarachnoid hemorrhage. Cardiac diseases and cerebrovascular diseases are the second and third causes of death in Japan, respectively. Such diseases cause substantial mortality and morbidity in many other countries as well, particularly in the more developed parts of the world. In the year 1998, sixty four patients per thousand in Japan visited the hospital regularly for hypertension according to research by the Ministry of Health and Welfare and hypertension is a primary cause of death.

As a countermeasure against the hypertension, a number of therapies have been developed, for instance development and use antihypertensive drugs such as diuretics, sympatholytic depressants, vasodilators and angiotensin converting enzyme inhibitors. These drugs are usually administered to patients diagnosed with a serious degree of hypertension.

On the other hand, treatments which generally improve health or contribute to a healthy lifestyle are indicated for patients with slight or serious hypertension. Such lifestyle changes or therapies include, dietary improvements or supplementation, stress reduction, therapeutic exercise and restriction of smoking and drinking. Improvement in dietary habits is of particular importance, as some foods may induce or contribute to hypertension. On the other hand selection of foods that provide hypotensive or anti-hypertensive effects may provide a positive overall benefit. Certain antihypertensive compounds or compositions have been identified and isolated from various food products.

While pharmaceutical medications and drugs generally act faster and exert a satisfactory anti-hypotensive effect than lifestyle or dietary changes, they often burden a patient with undesirable side-effects. On the other hand, while traditional food and nutritional products providing anti-hypertensive benefits are generally safe and free from substantial side-effects, the anti-hypertensive effects provided by these products may not always be satisfactory strong or efficacious, particularly in moderate or severe cases of hypertension, or the beneficial effects of such products may require a long time to develop.

Ferulic acid (3-(4-Hydroxy-3-methoxyphenyl)-2-propenoic acid ($C_{10}H_{10}O_4$) is widely distributed in small amounts in plants. It may be isolated according to the method of Batesmith, Chem. & Ind. (London) 1954, 1457 or Klosterman, Muggli, J. Am. Chem. Soc. 81, 2188 (1959). It may also be prepared by chemical synthesis, for example, a process by a condensation reaction of vanillin and malonic acid, Journal of American Chemical Society, 74, 5346, (1952). Ferulic acid has the following chemical structure:

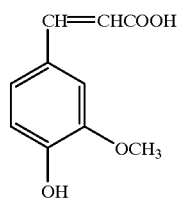

SUMMARY OF THE INVENTION

It is an object of the present invention to provide a drug, quasi-drug, pharmaceutical composition, or food or nutritional product which exerts a significantly high hypotensive effect, but which is safe, convenient to administer, and easily assimilated. The present inventors have discovered that ferulic acid and its derivatives, such as salts and esters of this compound exert a remarkable anti-hypertensive or hypotensive effect.

Additionally, it has been found that an even higher hypotensive effect can be achieved by a combining a ferulic acid derivative with a diglyceride. For instance by combining a diglyceride with a ferulic acid compound selected from the group consisting of ferulic acid, a salt of ferulic acid and a ferulic ester. Ferulic acid products either alone or in combination with diglycerides are advantageously incorporated into pharmaceutical, nutraceutical or other nutritional products, such as foods for treatment of diseases such as those associated with hypertension.

According to the present invention, there is thus provided a method of treating hypertension, which comprises administering ferulic acid or a salt thereof. The present invention also provides a method of treating hypertension, which comprises administering a composition containing:

(a) at least one ferulic acid compound, for instance selected from the group consisting of ferulic acid, a salt of ferulic acid and a ferulic ester and (b) a diglyceride.

An inventive fat composition is provided comprising:

(a) at least one ferulic acid compound selected from the group consisting of ferulic acid, a salt of ferulic acid and a ferulic ester and (b) a glyceride composition containing at least 15% by weight of a diglyceride.

According to the present invention, a ferulic acid compound may be taken by itself as the only active antihypertensive ingredient in a pharmaceutical composition or food, or alternatively in a composition containing a diglyceride. Either alone or in combination, such compositions suppress elevated blood pressure and reduce the effects of hypertension, thus improving the prognosis of diseases associated with hypertension. Additionally, ferulic acid compounds may be combined with other conventional medications for hypertension, or other hypotensive agents. Therefore, the products according to the present invention are useful as drugs and food for preventing and treating hypertension.

DETAILED DESCRIPTION OF THE PREFERRED EMBODIMENTS

Ferulic acid, and its derivatives, such as its salts and esters used in the present invention may be extracted from natural substances, particularly plants, containing them or industrially manufactured by chemical synthesis. Ferulic acid derivatives also encompass chemical compounds which are biotransformed or converted into ferulic acid when administered to a subject. Such derivatives also include biologically active hypotensive or anti-hypertensive compounds derived from a ferulic acid, its salts or esters when administered to a subject. Incidentally, stereoisomers exist in ferulic acid and its derivatives. However, all the isomers may be used, and mixtures of different isomers may also be used.

Ferulic acid may be extracted from plants such as coffee, onion, Japanese radish, lemon, *Cnidium ooficinale* Makino, *Angelica acutiloba*, pine, *Captis japonica* Makino, asafetida, sweet potato, corn, barley and rice, with rice being particularly preferred. The term "rice" in the present specification includes green or dried products of grain such as *Oryza sative* LINNE.

For the preparation of a ferulic ester, a rice bran oil is first prepared from rice bran, and then partitioned with hydrous ethanol and heat at room temperature under weakly alkaline conditions, thereby obtaining the ferulic ester in a hydrous ethanol fraction. Ferulic acid can be obtained by hydrolyzing the ferulic ester obtained by the above-described process with sulfuric acid with heating under pressure and purifying the resultant hydrolyzate or by culturing Pseudomonas in a medium containing clove oil from buds and leaves of *Syzygium aromaticum* MERRILL et PERRY by steam distillation, or eugenol obtained by purifying clove oil and subjecting the medium to isolation and purification.

The solubility of ferulic acid in water can be improved by providing it in the form of a salt, and its physiological effectiveness thus enhanced. No particular limitation is imposed on the salt of ferulic acid so far as it is a pharmaceutically acceptable salt. Examples of a basic substance used for forming such a salt include alkali metal hydroxides such as lithium hydroxide, sodium hydroxide and potassium hydroxide; alkaline earth metal hydroxides such as magnesium hydroxide and calcium hydroxide; inorganic bases such as ammonium hydroxide; basic amino acids such as arginine, lysine, histidine and ornithine; and organic bases such as monoethanolamine, diethanolamine and triethanolamine, with the alkali metal hydroxides and alkaline earth metal hydroxides being particularly preferred. The agents or fat compositions according to the present invention for preventing and treating hypertension may be formulated either by preparing such a salt and adding the salt to a composition composed of other components, or by separately adding ferulic acid and a salt-forming component to the above composition and forming a salt in the composition.

Examples of the alcohol moiety of the ferulic ester used in the present invention include linear or branched alkyl or alkenyl alcohols (preferably, linear or branched alkyl or alkenyl alcohols having 1 to 40 carbon atoms), aryl alcohols (preferably, aryl alcohols having 6 to 40 carbon atoms), terpene alcohols (particularly, monoterpene alcohol, sesquiterpene alcohol, diterpene alcohol and triterpene alcohol), sterol, trimethylsterol and plant sterol. More specifically, ethanol, oleyl alcohol, 2-ethylhexyl alcohol, allyl alcohol, cetyl alcohol, menthyl alcohol, phenol, benzyl alcohol, cholesterol, cycloartenol, 24-methylenecycloartenol, campesterol, β-sitosterol, stigmasterol, α-sitostanol, β-sitostanol and campestanol.

The combined use of a ferulic acid product such as one selected from the group consisting of ferulic acid, a salt of ferulic acid and a ferulic ester with a diglyceride permits further enhancing the hypotensive effect. As the diglyceride used herein, is preferred that having an acyl group having 8 to 24 carbon atoms, particularly 12 to 22 carbon atoms, for example, an acyl group derived from palmitic acid, stearic acid, oleic acid, linolic acid, linolenic acid, eicosapentaenoic acid or docosahexaenoic acid. The content of the unsaturated acyl group in the diglyceride is preferably at least 55% by weight (hereinafter indicated merely by "%"), particularly at least 70% based on the weight of the whole acyl group. The unsaturated fatty acid is most preferably composed of 15 to 85% of oleic acid and 15 to 85% of linolic acid. The diglyceride of such a constitution is liquid near the bodily temperature and has an effect of enhancing the solubility of products such as ferulic acid, or a salt or ester thereof.

The diglyceride can be obtained in accordance with the process described in Japanese Patent Application Laid-Open No. 300825/1992 or the like, for example, by an optional process such as a transesterification reaction of a triglyceride oil such as rapseed oil, soybean oil, rice bran oil, corn oil, palm oil, olive oil, perilla oil, sesame oil, linseed oil or fish oil with glycerol, or an esterification reaction of a fatty acid derived from a oil or fat with glycerol. Reaction processes include a chemical reaction process making use of an alkali catalyst or the like and a biochemical reaction process making use of a fat-hydrolyzing enzyme such as a lipase, and the like. However, it is preferable to use the biochemical reaction process to prevention of deterioration such as coloring.

In such a manner, the diglyceride is generally provided as a glyceride composition containing a monoglyceride and a triglyceride. The content of the diglyceride in the glyceride composition is preferably at least 15%, more preferably at least 55%, particularly preferably at least 80%. The hypotensive effect is enhanced by its combined use with ferulic acid, or a salt or ester thereof so far as the glyceride composition contains at least 15% of the diglyceride. The diglyceride content in the glyceride composition is preferably at most 95% from the viewpoint of manufacturing profitability of the diglyceride, while the content of the monoglyceride is preferably at most 2%, with the remainder being the triglyceride.

The fat composition comprising the glyceride composition containing at least 15% of the diglyceride and ferulic acid, or a salt or ester of ferulic acid is novel and can be widely used as not only a medicine for preventing and treating hypertension, but also a food or nutritional material. The content of ferulic acid, or the salt or ester thereof in the fat composition is preferably 0.01 to 50%, particularly preferably 0.1 to 20%.

The use of ferulic acid, or the salt or ester thereof or its combined use with a diglyceride can bring about an excellent hypotensive effect as demonstrated in the following Examples. These components are useful as drugs or nutraceuticals for preventing and treating hypertension and in food because they are highly safe.

Other hypotensive or anti-hypertensive drugs may be incorporated into the inventive compositions, nutraceuticals and foods and used in methods of treating hypertension, cardiac diseases and cerebrovascular diseases according to the present invention. Such drugs may include hypotensive drugs, for example, β-blockers, ACE inhibitors, Ca antagonists, diuretics, neurotropic drugs, etc.; various kinds of vitamins, for example, vitamin A, vitamin B1, B2, B6 and B12, vitamin C, vitamin D, vitamin E, etc.; and other active ingredients having a hypotensive or anti-hypertensive effect, for example, physiologically active lipids such as ω-3 type polyvalent unsaturated fatty acids such as α-linolenic acid, eicosapentaenoic acid and docosahexaenoic acid, or triglycerides containing any of these fatty acids as a constitutive fatty acid, etc., litchi, ginkgo, *Zizyphi fructus, Polygonatum sibiricum, cassiae semen*, shiitake, *Momordica grosvenori, Chrysanthemum morifolium, Plymnia sonchifolia*, mulberry leaves, banana leaves, *Curculigo orchioides*, plantago seed, *Corchorus olitorius*, etc.

When the composition according to the present invention is used as a medicine, a pharmaceutically acceptable carrier may be added to the above-described ingredients to prepare an oral or parenteral composition. Forms of the oral composition include tablets, granules, grains, pills, powder, capsules (including hard capsules and soft capsules), troches, chewable preparations and solutions (drinks). On the other hand, forms of the parenteral composition include those useful for intravenously administration, application to a mucous membrane or topical administration, such as injectable solutions, suppositories, and external skin care preparations.

When the composition according to the present invention is used as a food, the form of the food may be any forn such as liquid, emulsion or paste food such as juice, margarine, mayonnaise, milk or curry; semisolid food such as jelly, gelatin or gumi; solid food such as gum, bean curd or nutritional supplements; or powdered food or edible oil, to which conventional food additives are added in addition to the active ingredients.

The effective dose of ferulic acid, or the salt or ester thereof used in the present invention per day for an adult (body weight: 60 kg) is preferably 0.001 to 100 g, particularly 0.01 to 10 g per day. The effective dose of the diglyceride is preferably 0.1 to 70 g, particularly 0.1 to 40 g per day for an adult (body weight: 60 kg).

EXAMPLE 1

Composition of Soft Capsule

| | |
|---|---|
| Gelatin | 70.00% |
| Glycerol | 22.90 |
| Methyl p-hydroxybenzoate | 0.15% |
| Propyl p-hydroxybenzoate | 0.51% |
| Water | 6.44% |
| Total | 100.00% |

The soft capsule (oval form, weight: 150 mg) composed of the above composition was charged with soybean oil (450 mg) and ferulic acid (50 mg) in accordance with a conventional method to prepare a soft capsule preparation.

EXAMPLE 2

This example describes an emulsified drink containing a ferulic acid compound. The "oil and fat" component below comprises a glyceride composition (monoglyceride: 1.2%; diglyceride: 85.0%; and triglyceride: 13.8%) prepared from a fatty acid derived from rapeseed oil and glycerol using an enzymatic method.

| | |
|---|---|
| Oil and fat | 20.0% |
| Nonfat milk | 3.5% |
| Protein (casein) | 3.5% |

-continued

| | |
|---|---|
| Egg yolk lecithin | 0.7% |
| Fructose | 9.0% |
| Sodium ferulate | 1.0% |
| Citric acid | 0.1% |
| Ascorbic acid | 0.1% |
| Perfume base | 0.1% |
| Water | 62.0% |
| Total | 100.0% |

The drink having the above composition was found to have high emulsion stability and has desirable or acceptable organoleptic properties.

EXAMPLE 3

This example describes a wheat product (cookies) comprising a ferulic acid compound. The "oil and fat" component below comprises a glyceride composition (monoglyceride: 1%; diglyceride: 82%; and triglyceride: 17%) prepared from a fatty acid derived from rapeseed oil and glycerol using an enzymatic method.

| | |
|---|---|
| Oil and fat | 15.0 g |
| Corn starch | 20.0 g |
| Wheat | 50.0 g |
| Butter | 5.0 g |
| Fructose | 14.0 g |
| α-Sitosterol ferulate | 1.0 g |
| Sodium chloride | 0.5 g |
| Sodium bicarbonate | 0.5 g |
| Water | 10.0 g |

Cookies composed of the above composition were baked in accordance with conventional methods.

TEST EXAMPLE 1

Comparison of Short-term (1 hour) Hypotensive Effects Induced by Compositions Containing Ferulic Acid Compounds i) Experimental Materials and Method:

(a) Animals Used: Spontaneously Hypertensive Rats ("SHR"). Male.

The blood pressure of each spontaneous hypertensive rat (SHR) aged 15 weeks was preliminarily continuously measured for 7 days by means of a commercially available non-invasive sphygmomanometer (manufactured by Softron Co., Ltd.), thereby fully accustoming the rats to the sphygmomanometry, and an evaluation test was then started. All the rats were bred (in a breeding chamber in a rat zone) under conditions of a temperature of 25±1° C., a relative humidity of 55±10% and a lighting time of 12 hours (from 7 a.m. to 7 p.m.).

(b) Administration Method and Dose:

Compositions for Control Group and Test Groups 1 to 6 were prepared in accordance with their corresponding formulations shown in Table 1. Oral administration was adopted as an administration method, and the respective compositions were forcibly administered by means of a metal-made stomach tube. The dose was determined to be 15 mL/kg.

TABLE 1

| Component | Control Group | Test Group 1 | 2 | 3 | 4 | 5 | 6 |
|---|---|---|---|---|---|---|---|
| Ferulic Acid | — | 1.67 | — | 1.67 | — | — | 0.83 |
| Sodium ferulate | — | — | 1.67 | — | 1.67 | — | — |
| Cycloartenol ferulatte | — | — | — | — | — | 1.67 | 0.83 |
| Rapseed oil | 16.67 | 16.67 | 16.67 | — | — | — | — |
| Digylceride used in Example 2 | — | — | — | 16.67 | 16.67 | 16.67 | 16.67 |
| Lecithin | 0.8 | 0.8 | 0.8 | 0.8 | 0.8 | 0.8 | 0.8 |
| Water | 83.25 | 81.58 | 81.58 | 81.58 | 81.58 | 81.58 | 81.59 |
| Total | 100 | 100 | 100 | 100 | 100 | 100 | 100 |

(c) Testing Method:

Six SHRs aged 15 weeks caused to fast overnight were used as a group. The systolic blood pressure (SBP) of a tail artery of each rat was measured before the oral administration of the composition (emulsion) and after 1 hour from the administration.

(d) Statistical Processing Method:

The thus-obtained test results were expressed by a mean and standard error to conduct a Student's t-test. A level of significance was defined as at most 5%.

(ii) Results:

The systolic blood pressures in each group before the administration and after 1 hour from the administration are shown in Table 2. As apparent from Table 2, the blood pressure was significantly reduced in the groups (Test Groups 1 and 2) administered with ferulic acid or the salt thereof compared with Control Group. In the groups (Test Groups 3 to 6) administered with any one of these compounds or the ferulic ester and the diglyceride in combination, the hypotensive effect was more markedly developed.

TABLE 2

| | SBP (mmHg) | |
|---|---|---|
| | Before administration | After 1 hour from administration |
| Control Group | 204.2 ± 5.9 | 202.8 ± 4.5 |
| Test Group 1 | 206.0 ± 1.3 | 180.4 ± 2.5** |
| Test Group 2 | 207.1 ± 4.2 | 181.6 ± 4.1** |
| Test Group 3 | 207.2 ± 3.0 | 165.9 ± 3.6***,# |
| Test Group 4 | 209.5 ± 4.4 | 168.1 ± 2.5***,# |
| Test Group 5 | 208.5 ± 3.5 | 163.2 ± 1.2***,# |
| Test Group 6 | 205.5 ± 5.3 | 161.4 ± 4.1***,# |

,*There are significant differences at levels of significance of at most 1% and 0.1%, respectively.
There is a significant difference at a level of significance of at most 5% in other Test Groups as against Test Group 1.
Each value is expressed by mean ± standard error.

TEST EXAMPLE 2

Comparison of Long-term (4 weeks) Hypotensive Effects Induced by Compositions Comprising Ferulic Acid Compounds i) Experimental Materials and Method:

(a) Animal Used: Spontaneous Hypertensive Rats ("SHR"). Male.

The blood pressure of each spontaneous hypertensive rat (SHR) aged 5 weeks was preliminarily continuously measured for 7 days by means of a commercially available non-invasive sphygmomanometer (manufactured by Softlon Co.), thereby fully accustoming the rats to the sphygmomanometry, and an evaluation test was then started. All the rats were bred (in a breeding chamber in a rat zone) under conditions of a temperature of 25±1° C., a relative humidity of 55±10% and a lighting time of 12 hours (from 7 a.m. to 7 p.m.).

(b) Administration Method and Dose:

Rats of Test Groups 1 to 6 and Control group were provided as indicated in Test Example 1. Oral administration was adopted as an administration method, and the respective compositions were forcibly administered by means of a metal-made stomach tube. The dose was determined to be 10 mL/kg/day, and the administration was conducted for 5 days a week over 4 weeks.

(c) Testing Method:

Six SHRs aged 6 weeks were used as a group to measure the systolic blood pressure (SBP) of a tail artery of each rat before the test and after 4 weeks from the starting of the test.

(d) Statistical Processing Method:

The test results obtained were expressed by a mean and standard error and a Student's t-test was used to measure statistical significance of the results. A level of significance was defined as at most 5%.

(ii) Results:

Table 3 shows the systolic blood pressures (SBP) of each group before administration of a ferulic acid (or control) composition and after 4 weeks of five-times a week administration of these compositions. As apparent from Table 3, the rise of blood pressure was significantly inhibited in Test Groups 1 and 2 that were administered ferulic acid compositions compared with the Control Group. In Test Groups 3 to 6 administered with any one of the ferulic acid compounds or ferulic ester and the diglyceride in combination, the inhibitory effect on the rise of blood pressure was more markedly exhibited.

TABLE 3

| | SBP (mmHg) | |
|---|---|---|
| | Before administration | administration |
| Control Group | 145.2 ± 3.5 | 202.8 ± 4.5 |
| Test Group 1 | 145.2 ± 3.0 | 190.9 ± 2.8* |
| Test Group 2 | 145.1 ± 3.7 | 191.5 ± 3.6* |
| Test Group 3 | 145.3 ± 3.1 | 178.0 ± 3.5**,# |
| Test Group 4 | 145.6 ± 2.2 | 177.3 ± + 4.0**,# |
| Test Group 5 | 145.1 ± 2.9 | 174.1 ± 2.1**,# |
| Test Group 6 | 145.0 ± 2.8 | 166.8 ± 4.5***,# |

*,,*There are significant differences at levels of significance of at most 5%, 1% and 0.1%, respectively.
There is a significant difference at a level of significance of at most 5% in other Test Groups as against Test Group 1.
Each value is expressed by mean ± standard error.

Modifications and Other Embodiments

Various modifications and variations of the described methods and compositions and concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the chemical, medical or pharmaceutical arts or related fields are intended to be within the scope of the following claims.

Incorporation by Reference

Each reference, patent application or patent publication cited by or referred to in this disclosure is incorporated by reference in its entirety. Any patent document to which this application claims priority is also incorporated by reference in its entirety. Specifically, the foreign priority documents which are corresponding Japanese Patent Application 11-268461, filed Sep. 22, 1999, Japanese Patent Application 2000-107957, filed Apr. 10, 2000 and Japanese Patent Application 2000-230463, filed Jul. 31, 2000, are hereby incorporated by reference.

What is claimed is:

1. A composition comprising ferulic acid or a derivative thereof in a form and in amount suitable for treating a subject suffering from hypertension, wherein said composition further comprises a glyceride composition in which diglyceride is present in an amount of at least 15% by weight of the glyceride composition.

2. The composition of claim 1, wherein said ferulic acid or derivative thereof is selected from the group consisting of ferulic acid, a salt of ferulic acid and a ferulic ester.

3. A composition consisting essentially of ferulic acid or a derivative thereof, and a diglyceride, in a form and in amount suitable for treating a subject suffering from hypertension.

4. The composition of claim 3, wherein said ferulic acid or derivative thereof is selected from the group consisting of ferulic acid, a salt of ferulic acid and a ferulic ester.

5. A composition consisting essentially of ferulic acid or a derivative thereof, and at least one other anti-hypertensive compound, in a form and in amount suitable for treating a subject suffering from hypertension.

6. The composition of claim 5, wherein said ferulic acid or derivative thereof is selected from the group consisting of ferulic acid, a salt of ferulic acid and a ferulic ester.

7. A composition comprising ferulic acid or a derivative thereof, and a diglyceride, in a form and in amount suitable for treating a subject suffering from hypertension, wherein a triglyceride is optionally present in an amount less than the amount of the diglyceride.

8. The composition of claim 7, wherein said ferulic acid or derivative thereof is selected from the group consisting of ferulic acid, a salt of ferulic acid and a ferulic ester.

9. A method of treating hypertension comprising administering a composition comprising ferulic acid or a derivative thereof.

10. A method of treating hypertension comprising administering a composition comprising ferulic acid or a derivative thereof, and a diglyceride.

11. A method of treating a cardiac disease or a cerebrovascular disease comprising administering a composition consisting essentially of ferulic acid or a derivative thereof.

* * * * *